United States Patent
Heisel et al.

(10) Patent No.: US 10,307,148 B2
(45) Date of Patent: Jun. 4, 2019

(54) METHOD OF FORMING PERCUTANEOUS CATHETER DIRECTED COLLAPSIBLE MEDICAL CLOSURE DEVICE

(71) Applicant: St. Jude Medical, Cardiology Division, Inc., St. Paul, MN (US)

(72) Inventors: Jennifer Heisel, Princeton, MN (US); Kevin Joseph Schutt, Albertville, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 212 days.

(21) Appl. No.: 15/598,904

(22) Filed: May 18, 2017

(65) Prior Publication Data
US 2017/0252024 A1 Sep. 7, 2017

Related U.S. Application Data

(62) Division of application No. 13/793,289, filed on Mar. 11, 2013, now Pat. No. 9,681,861.

(51) Int. Cl.
*B21D 39/00* (2006.01)
*B21D 53/00* (2006.01)
(Continued)

(52) U.S. Cl.
CPC .......... *A61B 17/0057* (2013.01); *B21D 39/00* (2013.01); *B21D 53/00* (2013.01);
(Continued)

(58) Field of Classification Search
CPC ... B21D 39/00; B21D 53/00; Y10T 29/49968; A61B 17/0057; A61B 90/39;
(Continued)

(56) References Cited

U.S. PATENT DOCUMENTS 5,846,261 A 12/1998 Kotula et al.
2003/0057156 A1 3/2003 Peterson et al.
(Continued)

FOREIGN PATENT DOCUMENTS

EP 2387950 A1 11/2011
EP 2757962 A1 7/2014

OTHER PUBLICATIONS

International Search Report for Application No. PCT/US2013/078281, dated Apr. 22, 2014, 12 pages.

*Primary Examiner* — Jermie E Cozart
(74) *Attorney, Agent, or Firm* — Armstrong Teasdale LLP

(57) ABSTRACT

The present disclosure provides an improved collapsible medical closure device fabricated from a tubular wire mesh material. The collapsible medical closure device has an expanded preset configuration and an elongated collapsed reduced diameter configuration for delivery through a delivery catheter or other delivery means to a desired treatment site. The collapsible medical closure device is shaped to create short-term and long-term occlusion of an opening, such as an opening in the wall of the heart, and includes a disc shaped portion on a distal end, a cone shaped portion on a proximal end, a middle portion connecting the disc shaped portion and the cone shaped portion, and a center end screw for attaching a delivery cable located in the middle portion. The collapsible medical closure device additionally includes a therapeutic membrane for aiding in occlusion and promoting tissue growth, as well as one or more radiopaque marker bands.

14 Claims, 12 Drawing Sheets

(51) Int. Cl.
*A61B 17/00* (2006.01)
*A61B 90/00* (2016.01)

(52) U.S. Cl.
CPC ..... *A61B 90/39* (2016.02); *A61B 2017/00526* (2013.01); *A61B 2017/00592* (2013.01); *A61B 2017/00623* (2013.01); *A61B 2017/00628* (2013.01); *A61B 2017/00867* (2013.01); *A61B 2090/3966* (2016.02); *Y10T 29/49968* (2015.01)

(58) Field of Classification Search
CPC .. A61B 2090/3966; A61B 2017/00526; A61B 2017/00592; A61B 2017/00623; A61B 2017/00628; A61B 2017/00867
See application file for complete search history.

(56) References Cited

U.S. PATENT DOCUMENTS

| | | |
|---|---|---|
| 2004/0254594 A1 | 12/2004 | Alfaro |
| 2007/0233186 A1 | 10/2007 | Meng |
| 2007/0265656 A1 | 11/2007 | Amplatz et al. |
| 2009/0099647 A1 | 4/2009 | Glimsdale et al. |
| 2009/0187214 A1 | 7/2009 | Amplatz et al. |
| 2009/0281567 A1 | 11/2009 | Osypka |
| 2011/0046662 A1 | 2/2011 | Moszner et al. |
| 2011/0082495 A1 | 4/2011 | Ruiz |
| 2012/0035643 A1* | 2/2012 | Khairkhahan ..... A61B 17/0057 606/194 |
| 2012/0065667 A1 | 3/2012 | Javois |
| 2012/0071918 A1 | 3/2012 | Amin |
| 2013/0131717 A1 | 5/2013 | Glimsdale |
| 2013/0296912 A1 | 11/2013 | Ottma |

\* cited by examiner

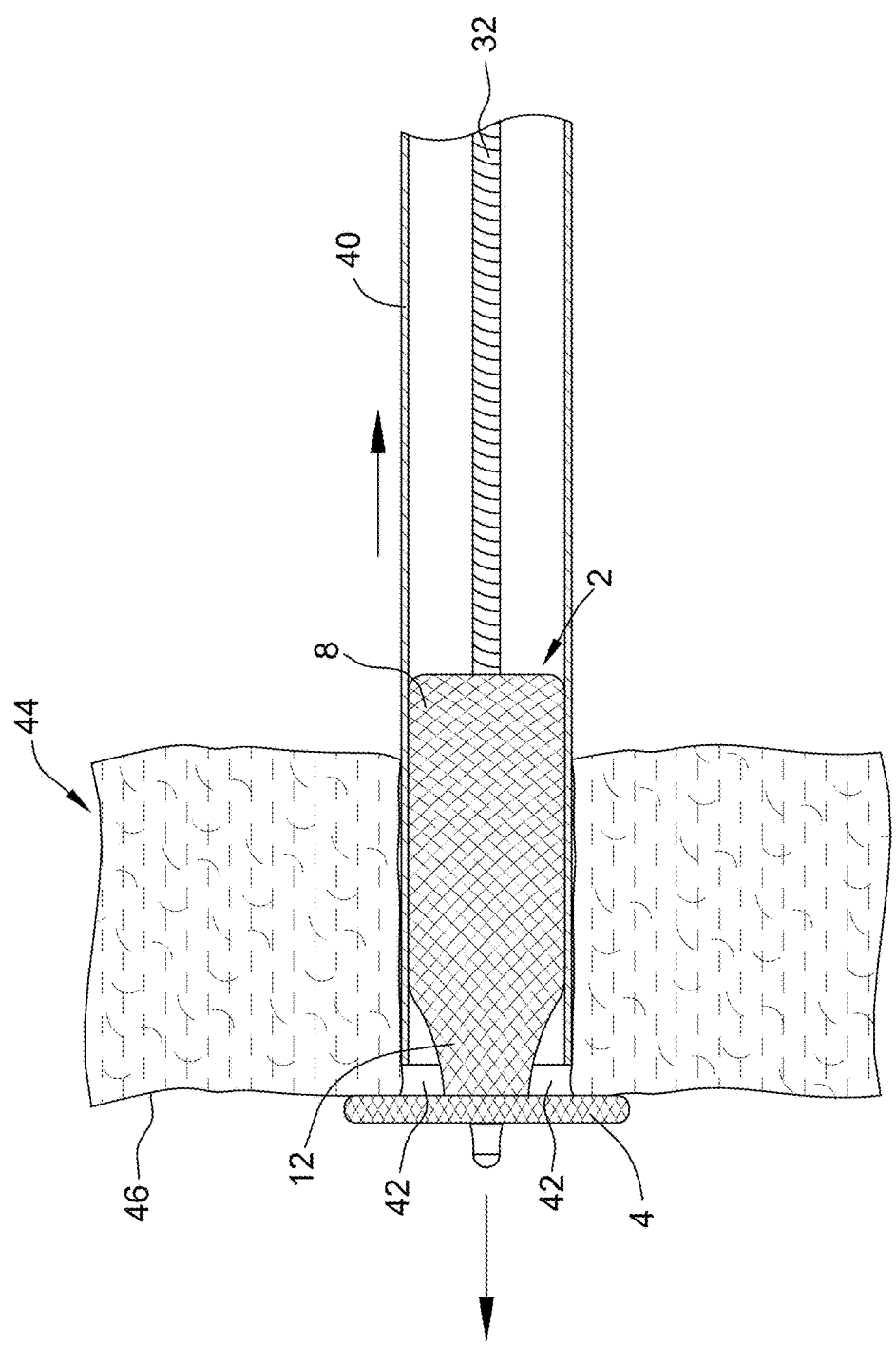

METHOD OF FORMING PERCUTANEOUS CATHETER DIRECTED COLLAPSIBLE MEDICAL CLOSURE DEVICE

CROSS-REFERENCE TO RELATED APPLICATIONS

The present application is a divisional of U.S. patent application Ser. No. 13/793,289, filed on Mar. 11, 2013, the contents of which are incorporated in their entirety herein by reference.

BACKGROUND OF THE DISCLOSURE a. Field of the Disclosure

The present disclosure generally relates to a medical occlusion device. In particular, the present disclosure relates to a percutaneous catheter directed collapsible medical closure device suitable for use as an occlusion device when rapid occlusion is desirable followed by long-term occlusion.

b. Background Art

It is well known that a number of desirable medical procedures in use today require access to the left ventricle of the heart. In the event that the vascular system is compromised, access to the left ventricle can be accomplished through percutaneous apical access. A catheter and guidewire are generally used to deliver fluids or other medical devices to the desired area. One specific procedure that utilizes percutaneous apical access is transcatheter aortic valve implantation, which is a treatment for severe aortic stenosis wherein an artificial aortic heart valve attached to a wire frame is guided by a catheter to the desired location in the heart.

Conventionally, transapical closure has been completed using a series of purse string sutures that are pulled tight and manually sewn in by a physician performing the procedure. Although this closure method has been generally successful in closing the hole or channel, it is labor intensive and time consuming. Additionally, the success rate for the outcome is physician dependent, and the quality of occlusion may vary from one physician to another based on experience.

SUMMARY OF THE DISCLOSURE

The present disclosure is directed to a collapsible medical closure device for occluding an opening in a body. The collapsible medical closure device comprises a disc shaped portion on a distal end, a cone shaped portion on a proximal end, a middle portion connecting the disc shaped portion and the cone shaped portion, and a means for attaching a delivery device to the collapsible medical closure device located in the middle portion. The disc shaped portion, cone shaped portion, and middle portion comprise a metal fabric, and at least a portion of the metal fabric is contacted by a therapeutic membrane.

The present disclosure is further directed to a method of forming a collapsible medical closure device. The method comprises (a) introducing a radiopaque marker band onto one end of a tubular metal fabric formed from a plurality of metal strands being formed from a material that can be heat treated to substantially set a desired shape; (b) introducing a means for attaching a delivery device inside of the radiopaque marker band; (c) inverting the tubular metal fabric over itself; (d) conforming the inverted tubular metal fabric to an internal surface of a molding element, wherein the molding element includes a disc shaped portion, a middle portion, and a cone shaped portion; (e) heating the inverted tubular metal fabric; (f) removing the tubular metal fabric from the molding element, whereby the tubular metal fabric defines the collapsible medical closure device having a disc shaped portion, a cone shaped portion, and a middle portion connecting the cone shaped portion and disc shaped portion, wherein the middle portion contains the means for attaching a delivery device; and (g) contacting a therapeutic membrane with the tubular metal fabric.

The present disclosure is further directed to a collapsible medical closure device comprising a metal fabric and a therapeutic membrane contacting at least a portion of the metal fabric. The metal fabric comprises woven metal strands having an expanded preset configuration shaped to create an occlusion of an opening in a body. The expanded preset configuration comprises a disc shaped portion having a first diameter on a distal end, a cone shaped portion having a second diameter on a proximal end, and a middle portion connecting the disc shaped portion and cone shaped portion. The middle portion contains a means for attaching a delivery device. The collapsible medical closure device is deformable through a channel in a patient's body. The woven metal strands have a memory property whereby the collapsible medical closure device tends to return to said expanded preset configuration when unconstrained.

BRIEF DESCRIPTION OF THE DRAWINGS

FIGS. 7A-7C are schematic views of the collapsible medical closure device of FIG. 1 being loaded and inserted into a heart wall.

DETAILED DESCRIPTION OF THE DISCLOSURE

Figure 1:
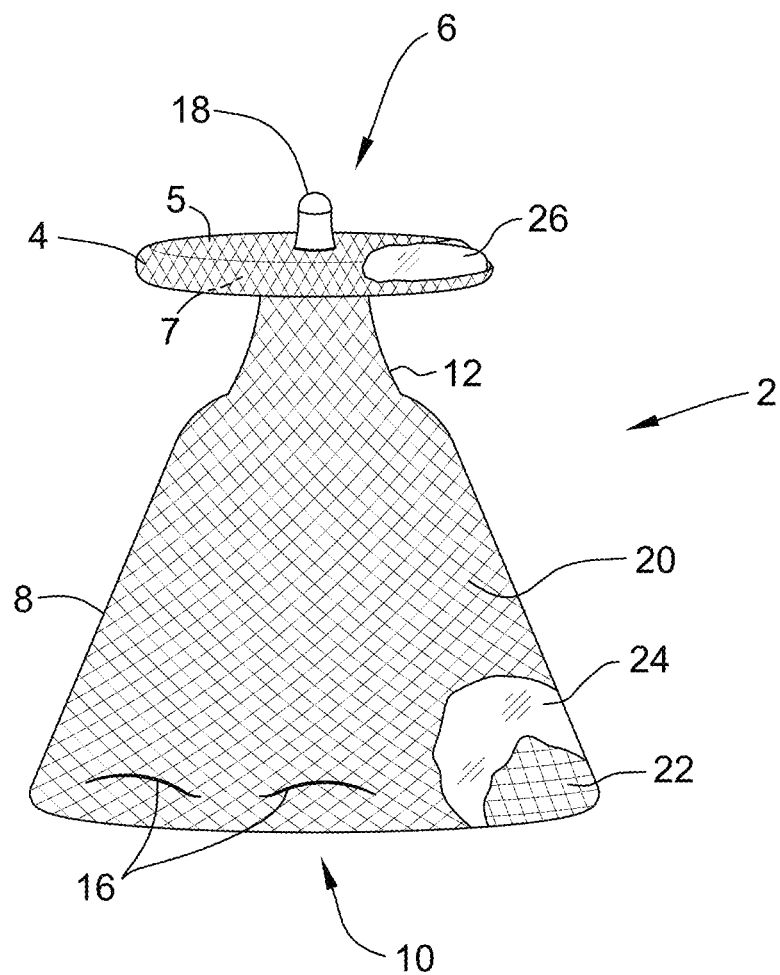
FIG. 1 depicts a perspective view of a collapsible medical closure device of the present disclosure with portions cut away to reveal internal construction.

It is desirable to be able to provide a medical device that can provide both short-term and long-term occlusion of holes or channels, especially those in the wall of the heart, without the risk of pericardial effusions or other complications. It is also desirable to provide methods of forming such medical devices. The present disclosure is directed to a collapsible medical closure device, and methods of forming and using the collapsible medical closure device, that is well suited for the selective short-term and long-term occlusion of a hole or channel in the wall of the heart.

The collapsible medical closure device is designed for delivery to the desired area through a delivery catheter or the like. The collapsible medical closure device includes a therapeutic membrane for increasing occlusion that contacts at least of portion of a metal fabric comprising the collapsible medical closure device that includes woven metal strands shaped into a disc shaped portion on a distal end, a cone shaped portion on a proximal end, and a middle portion connecting the cone shaped portion and the disc shaped portion and including an attachment means for attaching a delivery cable or other delivery device for delivering the collapsible medical closure device into the body. In many embodiments, the therapeutic membrane is sandwiched between layers of metal fabric. The collapsible medical closure device also desirably includes one radiopaque marker band in the middle portion and another radiopaque marker band on the disc shaped portion on the distal end.

When the collapsible medical closure device is inserted into the hole or channel, the disc shaped portion prevents the device from embolizing and provides a surface for occlusion on the endocardium that results in long-term closure, while the cone shaped portion prevents embolism and enhances both short-term and long-term occlusion. The therapeutic membrane aids in the initial occlusion and also promotes both long-term tissue growth and device stability. The collapsible medical closure device results in improved patient safety by reducing procedure time, reducing the risk of procedure bleeding, increasing procedure reproducibility, and reducing the size of the required thoracotomy.

The collapsible medical closure device is formed into a predetermined shape as described herein and may be inserted into a delivery catheter, or other delivery device, in a collapsed configuration. The collapsible medical closure device is advanced through the delivery catheter and out a distal end of the delivery catheter at a desired treatment site at which time, due to its memory properties as discussed herein, it will tend to substantially return to its expanded state and provide the benefits described herein.

The collapsible medical closure devices described herein are designed to be compatible with multiple commercially available delivery systems so that they may be delivered through the same delivery system being used for the initial procedure being performed to reduce procedural complication, which can result in less blood loss to the patient. Additionally, the collapsible medical closure devices are designed to be acutely recapturable so that in the event the device is undersized or oversized for the desired use, or is not positioned correctly, it can be easily recaptured and removed or repositioned such that an appropriately sized device can be used and placed in the proper position at the treatment site.

It has been unexpectedly found that a collapsible medical closure device including a disc shaped portion on a distal end, a cone shaped portion on a proximal end, a middle portion connecting the disc shaped portion and cone shaped portion, and a therapeutic membrane contacting at least a part of the collapsible medical closure device complies with a hole, channel, or opening in the body, such as a hole, channel, or opening in the wall of the heart, without holding the hole open and can provide both short-term and long-term occlusion. Surprisingly, the collapsible medical closure device having the disc shaped portion, cone shaped portion, and middle portion remains in the desired location in the hole or channel despite pressure from the inside of the ventricle and the force exerted by the beating heart. The disc shaped portion of the collapsible medical closure device has been found to provide a surface that contacts the inside of the endocardium and prevents the collapsible medical closure device from being pushed out of the hole, while the cone shaped portion is shaped so that the collapsible medical closure device has a tendency to pull the disc shaped portion close to the wall and prevents it from embolizing into the left ventricle, while still providing desired occlusion properties. The middle portion provides desirable flexibility to the collapsible medical closure device. The overall design of the presently disclosed collapsible medical closure device leads to improved patient outcomes and improved patient safety.

Figure 2:
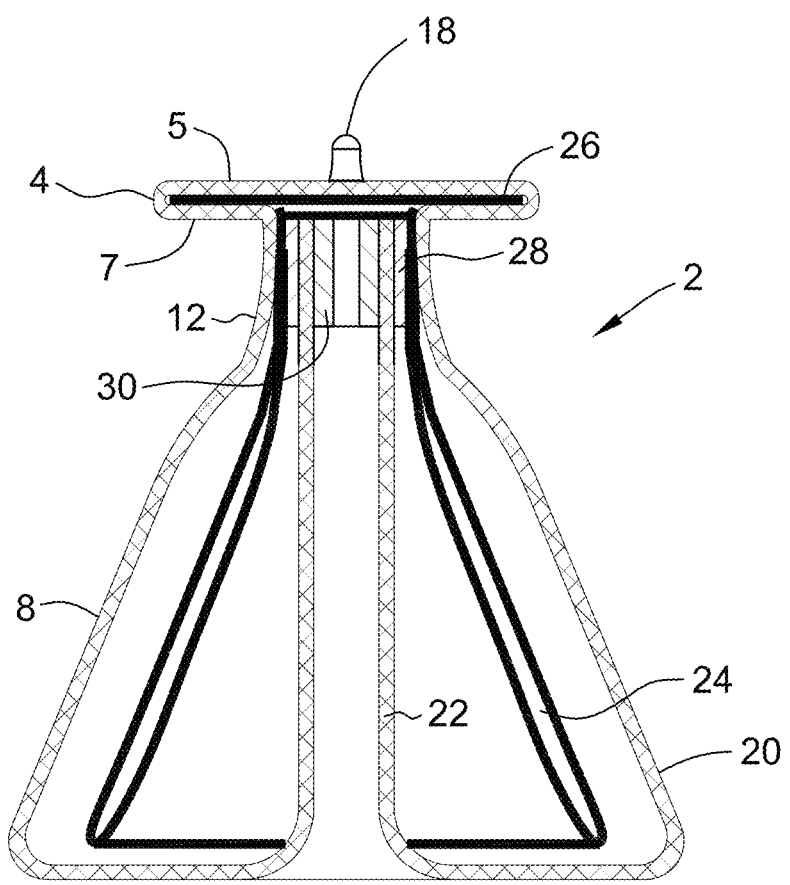
FIG. 2 is a schematic cross-section of the collapsible medical closure device of FIG. 1.

Turning to the figures, FIGS. 1 and 2 illustrate one embodiment of a collapsible medical closure device of the present disclosure, with FIG. 1 showing a perspective view of collapsible medical closure device 2 including portions cut away to reveal internal construction and FIG. 2 showing a cross section of collapsible medical closure device 2 to reveal internal construction.

Referring now to FIG. 1, there is shown collapsible medical closure device 2 in accordance with one embodiment of the present disclosure. Collapsible medical closure device 2 includes disc shaped portion 4 on distal end 6, cone shaped portion 8 on proximal end 10, middle portion 12, proximal end therapeutic membrane 24, distal end therapeutic membrane 26, sewing thread 16, and first radiopaque marker band 18. As illustrated, disc shaped portion 4 is disposed at one end of middle portion 12 and cone shaped portion 8 is disposed at the other end of middle portion 12 such that middle portion 12 joins together disc shaped portion 4 and cone shaped portion 8. Cone shaped portion 8 and middle portion 12 of collapsible medical closure device 2 includes first layer of metal fabric 20 and second layer of metal fabric 22. Further, disc shaped portion 4 includes top layer of metal fabric 5 and bottom layer of metal fabric 7. As discussed further herein, first layer of metal fabric 20, second layer of metal fabric 22, top layer of metal fabric 5 and bottom layer of metal fabric 7 are formed during manufacturing of collapsible medical closure device 2 from a single layer of metal fabric that is inverted upon itself, molded, and heat set into the desired configuration as described below.

As shown in FIG. 1, first layer of metal fabric 20 and second layer of metal fabric 22 include woven metal strands that provide the structure of cone shaped portion 8 and middle portion 12 of collapsible medical closure device 2. Top layer of metal fabric 5 and bottom layer of metal fabric 7 include woven metal strands that provide the structure of disc shaped portion 4 of collapsible medical closure device 2.

The woven metal strands are a plurality of conventional wire strands that have a predetermined relative orientation between the strands. The metal strands define two sets of essentially parallel generally helical stands, with the strands of one set having a "hand", i.e., a direction of rotation, opposite that of the other set. These helical strands define a generally tubular metal fabric, known in the metal fabric industry as a tubular braid.

The pitch of the wire strands (i.e., the angle defined between the turns of the wire and the axis of the braid) and the pick of the fabric (i.e., the number of wire crossovers per unit length) may be adjusted as known by those of skill in the art to increase/decrease/optimize the rigidity/strength as desired for a particular application. The wire strands of the metal fabric used to construct collapsible medical closure device 2 are desirably formed of a material that is both resilient and that can be heat treated to substantially set a desired shape. Materials that are suitable for this purpose include a cobalt-based low thermal expansion alloy referred to in the field as Elgeloy, nickel-based high temperature high-strength superalloys commercially available from Haynes International under the trade name Hastelloy, nickel-based heat treatable alloys sold under the name Incoloy by International Nickel, and a number of different grades of stainless steel. The important factor in choosing a suitable material for the wires is that the wires retain a suitable amount of the deformation induced by a molding process (described hereinbelow) when subjected to a predetermined heat treatment.

One class of materials that are desirable is memory-shape alloys. Such alloys tend to have a temperature induced phase change that will cause the material to have a preferred configuration that can be fixed by heating the material above a certain transition temperature to induce a change in the phase of the material. When the alloy is cooled back down, the alloy will "recall" the shape it was in during the heat treatment and will tend to assume that configuration unless constrained from doing so.

One particularly desirable memory shape alloy for use in the present disclosure is nitinol, an approximately stoichiometric alloy of nickel and titanium, which may also include minor amounts of other metals to achieve desired properties. Nickel-titanium alloys are very elastic and are commonly referred to as "superelastic" or "pseudoelastic." The elasticity of these alloys helps a medical device return to an expanded configuration for deployment inside of the body following passage in a distorted or collapsed form through a delivery catheter. Nitinol is a particularly desirable alloy for forming the collapsible medical closure devices of the present disclosure.

The metal wires used to fabricate the collapsible medical closure devices of the present disclosure may include wires having a diameter of from about 0.002 to about 0.005 inches (about 0.051 to about 0.127 millimeters), desirably in the range of from about 0.003 to about 0.0035 inches (about 0.076 to about 0.089 millimeters), and in some embodiments, about 0.003 inches (about 0.076 millimeters). The number of wires in a wire mesh fabric (or tubular braid) may vary from about 36 to about 144, desirably from about 72 to about 144, and in some embodiments, 144. The pick count of the wire mesh may vary from about 30 to about 100, including from about 50 to about 80, including 70. As noted, the wire diameter and the number of wires in the wire mesh fabric will tend to influence the rigidity, strength, and flexibility of the collapsible medical closure device. Numerous other embodiments are contemplated within the scope of this disclosure. These combinations have been found to provide an appropriate combination of strength, rigidity, and flexibility for the medical closure device. In some embodiments, the metal fabric may be a bioabsorbable metal fabric.

As shown in FIG. 2, collapsible medical closure device 2 also includes second radiopaque marker band 28 and center end screw 30, both located in middle portion 12. Second radiopaque marker band 28 is positioned about the outer portion of second layer of metal fabric 22, and center end screw 30 is positioned about the inner portion of second layer of metal fabric 22.

First radiopaque marker band 18 and second radiopaque marker band 28 of collapsible medical closure device 2 allow for visibility of collapsible medical closure device 2 under an x-ray fluoroscope spectroscopy. Generally, each of first and second radiopaque marker bands 18 and 28 will be a thin-walled metal tube or ring, and may be made from a high density metal such as platinum, gold, tantalum and/or iridium. In one specific embodiment, first radiopaque marker band 18 and second radiopaque marker band 28 are comprised of a platinum/iridium metal alloy.

Center end screw 30 located in middle portion 12 of collapsible medical closure device 2 is an attachment means for attaching a delivery cable (shown in FIGS. 4 and 5 below) or other delivery device such that collapsible medical closure device 2 can be delivered into a body, and recaptured and removed or redeployed, if necessary. Although center end screw 30 or another threadable member attachment means is generally suitable, other non-threadable attachment means, such as magnetic attachment means, are also within the scope of the present disclosure. Center end screw 30 may generally be constructed of any suitable metal, including for example, stainless steel.

Collapsible medical closure device 2 as described herein includes a biodegradable therapeutic membrane, biodegradable therapeutic scaffold, or biodegradable therapeutic sponge (referred to herein collectively as a "therapeutic membrane"). This therapeutic membrane contacts at least a portion of collapsible medical closure device 2, and desirably, contacts substantially all of collapsible medical closure device 2, including disc shaped portion 4, middle portion 12, and cone shaped portion 8. As shown in FIGS. 1 and 2, the therapeutic membrane may consist of proximal end therapeutic membrane 24 and distal end therapeutic membrane 26. Distal end therapeutic membrane 26 is disc-shaped and is positioned between top layer of metal fabric 5 and bottom layer of metal fabric 7 of disc shaped portion 4. Proximal end therapeutic membrane 24 is generally cone shaped with an elongated portion extending from the top of the cone for positioning within cone shaped portion 8 and middle portion 12 and between first layer of metal fabric 20 and second layer of metal fabric 22 of collapsible medical closure device 2. This positioning enables proximal and distal end therapeutic membranes 24 and 26 to be held in place during placement of collapsible medical closure device 2 into the body as well as after placement such that proximal and distal end therapeutic membranes 24 and 26 can provide their intended occlusion function. In another embodiment, proximal and distal end therapeutic membranes 24 and 26 may be formed of a single, one piece therapeutic membrane. The present disclosure also contemplates collapsible medical closure devices having three, four, or more layers of therapeutic membranes contacting any portion or substantially all of collapsible medical closure device 2.

Proximal end therapeutic membrane 24 may be secured to first layer of metal fabric 20 and/or second layer of metal fabric 22 and distal end therapeutic membrane 26 may be secured to top layer of metal fabric 5 and/or bottom layer of metal fabric 7 by sewing thread 16 (shown in FIG. 1), by inserting the edges of proximal end therapeutic membrane 24 and distal end therapeutic membrane 26 into the picks of the wire fabric (not shown in FIGS. 1 and 2), or by a combination thereof to increase the stability of the membrane and device. Many suitable thread materials are commercially available, including several types of suitable polyester threads.

Suitable therapeutic membranes for use in collapsible medical closure device 2 will desirably provide both short-term and long-term benefits. Regarding the short-term benefits, the therapeutic membrane will desirably have an immediate impact on occlusion upon application; that is, the therapeutic membrane will, upon application to the desired area, immediately provide an occlusive benefit. For this acute occlusion, a semi-nonporous/nonporous membrane is desirable. For long-term occlusion and tissue ingrowth, a bioabsorbable membrane or a fabric that promotes cell seeding and tissue growth is desirable such that long-term device stability and closure is facilitated. Suitable membranes that provide both short-term and long-term benefits include, for example, polyester fabric, polyester fabric coated in elastin, polyester fabric coated in collagen, collagen sponge, collagen scaffolds made from a mixture of hydrogel and collagen, and mixtures thereof. Generally, it is desirable for the therapeutic membrane to include collagen.

The overall geometry of collapsible medical closure device 2 is important as it impacts the stability and function of collapsible medical closure device 2 once it is placed in the body. Collapsible medical closure device 2 should desirably comply with the hole or channel in the heart wall or other structure without holding the hole or channel open; however, collapsible medical closure device 2 should simultaneously remain in the desired location upon insertion despite the pressure from inside the ventricle and the force exerted by the beating heart. Disc shaped portion 4 of collapsible medical closure device 2 of the present disclosure provides a surface that contacts the inside of the endocardium and prevents collapsible medical closure device 2 from being pushed out of the hole or channel. Thus, collapsible medical closure device 2 closes the hole or channel on the endocardium without impeding normal cardiac function. Disc shaped portion 4 is desirably sized to be somewhat larger than the hole to be occluded to keep the collapsible medical closure device in the desired location.

Cone shaped portion 8 on proximal end 10 of collapsible medical closure device 2 is designed to prevent embolism while enhancing both short-term and long-term occlusion. The shape of cone shaped portion 8 is such that once collapsible medical closure device 2 is inserted into the wall of the heart or other structure (as discussed in more detail below), cone shaped portion 8 has a tendency to pull disc shaped portion 4 close to the wall of the heart and prevent it from embolizing into the left ventricle. Cone shaped portion 8 of collapsible medical closure device 2 sits inside of the open channel or hole upon application and after insertion of the collapsible medical closure device. When this channel closes around and engulfs/squeezes cone shaped portion 8 of collapsible medical closure device 2 after insertion and during the healing process, it tends to conform to the cone geometry. This conformity pulls disc shaped portion 4 up against the wall of the inside of the heart. This assists in not only sealing the hole from the inside, but also in closing off the channel and providing for long-term occlusion and tissue growth.

Middle portion 12 imparts overall flexibility to collapsible medical closure device 2, and more specifically, provides flexibility with respect to the movement of disc shaped portion 4 and cone shaped portion 8 relative to each other. This flexibility is important as it allows for independent movement of either disc shaped portion 4 or cone shaped portion 8 without substantially influencing the non-moving portion of collapsible medical closure device 2. This may be important based on varying anatomic heart structures. As such, collapsible medical closure device 2 is more adaptable for use with varying structural configurations inside of a body as it has substantial flexibility provided by middle portion 12.

Figure 3:
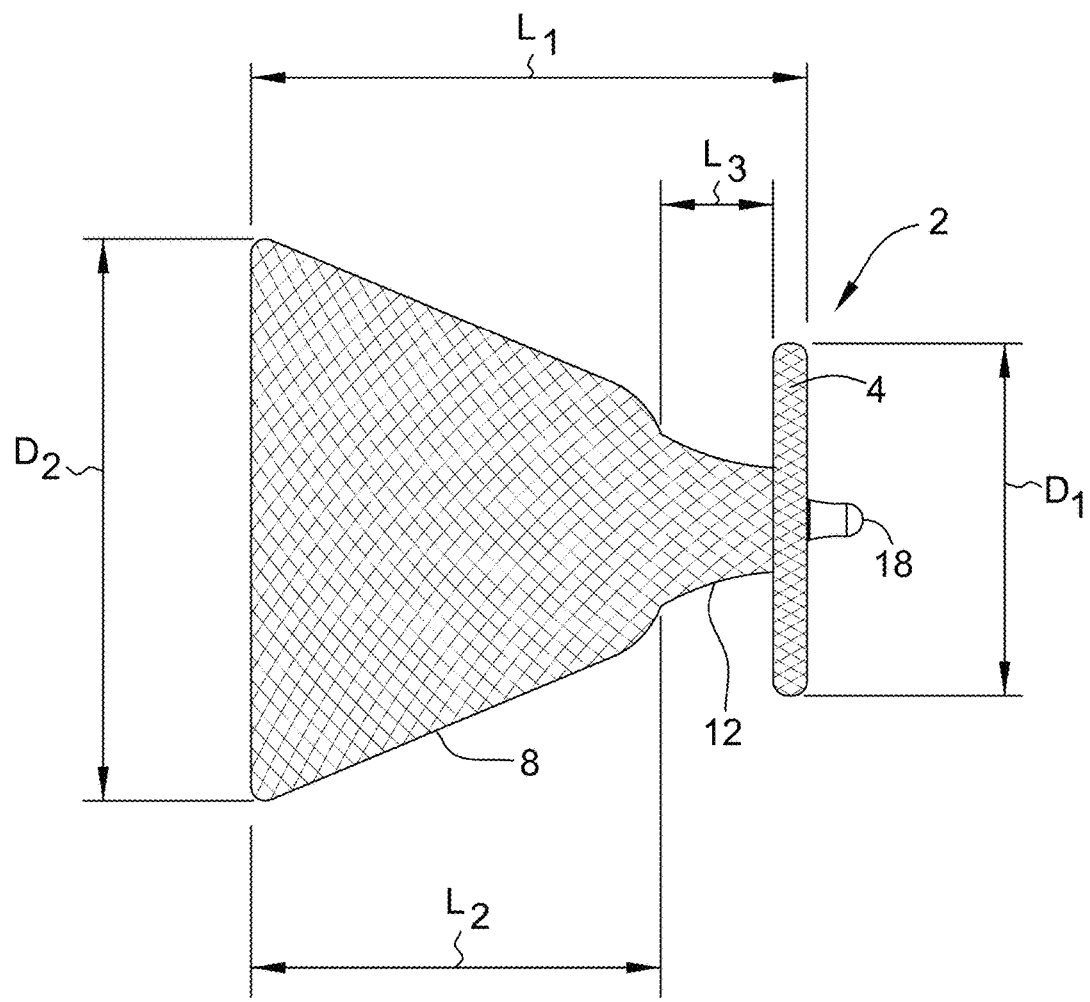
FIG. 3 depicts a side view of the collapsible medical closure device of FIG. 1.

FIG. 3 depicts collapsible medical closure device 2 from FIGS. 1 and 2 having length L1 and disc shaped portion 4 having diameter D1. Also shown is middle portion 12 having length L3, cone shaped portion 8 having diameter D2 and length L2, and first radiopaque marker band 18.

As shown in FIG. 3, collapsible medical closure device 2 has length L1, which is desirably chosen such that upon insertion into a hole or channel in the heart wall, such as a hole or channel created during a procedure that requires access to the left ventricle, or hole or channel in another structure, collapsible medical closure device 2 is sized and configured such that cone shaped portion 8 of collapsible medical closure device 2 does not protrude out of the hole or channel. Stated another way, collapsible medical closure device 2 has a length that is desirably sized and configured such that when implanted into the desired area, cone shaped portion 8 is either flush with the hole or channel, or slightly recessed therein so that no portion of cone shaped portion 8 "sticks out" from the hole or channel. Through this design, the potential for epicardial effusion is substantially reduced or eliminated as contact is minimized or eliminated. Generally, length L1 of collapsible medical closure device 2 will be from about 8 millimeters to about 16 millimeters, including from about 9 millimeters to about 15 millimeters, including from about 8 millimeters to about 14 millimeters. The exact length L1 of collapsible medical closure device 2 may, in some embodiments, be determined based on the heart wall thickness of the patient, which may typically be from about 10 millimeters to about 14 millimeters.

Also as shown in FIG. 3, cone shaped portion 8 has length L2 and middle portion 12 has length L3, both of which are shorter than length L1. Length L2 of cone shaped portion 8 will vary depending upon the overall length L1 of collapsible medical closure device 2 which, as noted above, will vary depending upon the wall thickness to be occluded. Cone shaped portion 8 generally has length L2 of from about 8 millimeters to about 14 millimeters, including from about 7 millimeters to about 13 millimeters. Middle portion 12 generally has a length L3, which will also vary depending on the overall length L1 of collapsible medical closure device 2. In general, length L3 is such that substantially all of second radiopaque marker band 28 with center end screw 30 inserted therein (as shown in FIG. 2) is positioned within middle portion 12. Middle portion 12 generally has a length L3 of from about 1 millimeter to about 4 millimeters, including from about 1 millimeter to about 3 millimeters, including from about 2 millimeters to about 4 millimeters, including from about 2 millimeters to about 3 millimeters. Such suitable lengths for L3 provide desired flexibility to collapsible medical closure device 2 as noted herein.

FIG. 3 also shows that cone shaped portion 8 has diameter D2 and disc shaped portion 4 has diameter D1. Diameter D1 is generally dependent upon the size of the hole to be occluded and, as noted above, is generally sized slightly larger than the hole to be occluded such that disc shaped portion 4 will remain properly positioned after placement. Because the holes or openings generally made from transapical procedures are slits having a 20-26 Fr opening, disc shaped portion 4 will desirably have diameter D1 of from about 5 millimeters to about 12 millimeters, including from about 6 millimeters to about 12 millimeters, including from about 7 millimeters to about 10 millimeters, including about 9 millimeters. Such sizing provides a sufficiently sized disc for occluding the hole or channel without impacting heart function. As will be recognized by one skilled in the art based on the disclosure herein, when the opening to be occluded is sized differently than a 20-26 Fr opening, disc shaped portion 4 may be sized appropriately.

Diameter D2 of cone shaped portion 8 as also shown in FIG. 3 is also partially dependent upon the size of the opening to be occluded. Cone shaped portion 8 is deformed during use due to the hole or opening closing around it as described above, and it will typically have diameter D2 of from about 6 millimeters to about 12 millimeters, including from about 6 millimeters to about 10 millimeters. The exact dimensions of collapsible medical closure device 2 may vary depending upon the size of the hole required for closure and the patient's wall thickness.

The above-mentioned sizes and configurations of cone shaped portion 8 of collapsible medical closure device 2 are, as noted above, selected such that cone shaped portion 8 on proximal end 10 does not protrude outside of the hole or channel to be occluded; that is, the collapsible medical closure device is sized and configured such that cone shaped portion 8 remains entirely inside of the channel upon application. By sizing and configuring collapsible medical closure device 2 in this way, no part of cone shaped portion 8 of collapsible medical closure device 2 protrudes out of the channel. As discussed, this significantly reduces or eliminates contact and interaction with the pericardium and as such reduces or eliminates the potential for late stage pericardial effusion. Further, by sizing and configuring disc shaped portion 4 in the manner described, a sufficiently sized disc is provided for occluding the hole or channel without impacting heart function. In addition, disc shaped portion 4 is also desirably limited in size as the endocardial surface of the left ventricle near the apex has a significant amount of trabeculi and the space at the apex is limited. By limiting the size of disc shaped portion 4, collapsible medical closure device 2 conforms better overall to the wall of the heart, without obstructing overall heart function.

Figure 4:
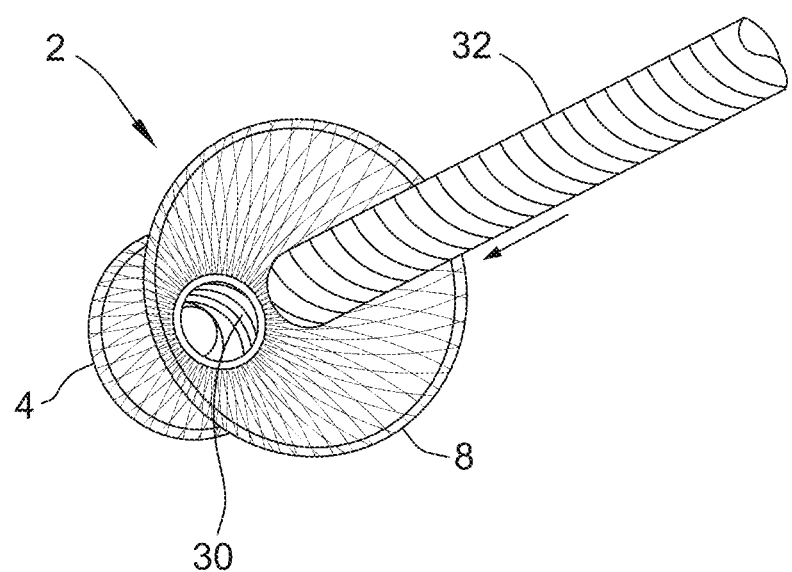
FIG. 4 is a view of the collapsible medical closure device of FIG. 1 down a cone shaped portion of the collapsible medical closure device.

Referring now to FIG. 4, which is collapsible medical closure device 2 of FIG. 1 as viewed down cone shaped portion 8 of collapsible medical closure device 2, there is shown collapsible medical closure device 2, cone shaped portion 8, disc shaped portion 4, center end screw 30, and delivery cable 32. As discussed above, center end screw 30 is generally positioned in middle portion 12 (not shown) of collapsible medical closure device 2 that connects cone shaped portion 8 and disc shaped portion 4 such that delivery cable 32 may access center end screw 30 through cone shaped portion 8. Center end screw 30 may be attached to collapsible medical closure device 2 by a circumferential weld (not shown) about a circumference of center end screw 30 as detailed below. More specifically, as discussed in more detail below, center end screw 30 is positioned within second radiopaque marker band 28 and second layer of metal fabric 22 (shown in FIG. 2) such that center end screw 30, second layer of metal fabric 22 and second radiopaque marker band 28 will all be welded together or otherwise affixed together about the circumference of second radiopaque marker band 28 and center end screw 30. Center end screw 30 is designed and configured for threadable engagement with delivery cable 32, which is designed and configured to screw or thread into center end screw 30 for delivery of collapsible medical closure device 2 into a patient. Delivery cable 32 can take any suitable shape, but may desirably be an elongated flexible metal shaft similar to a conventional guidewire or may be a hollow shaft.

Figure 5:
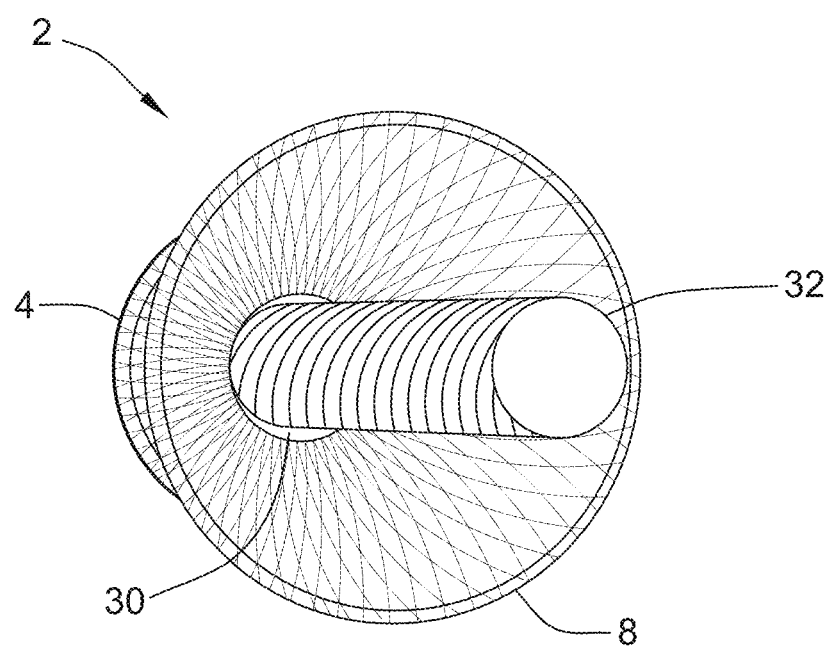
FIG. 5 is a view of the collapsible medical closure device of FIG. 1 down a cone shaped portion of the collapsible medical closure device including an attached delivery cable.

Turning now to FIG. 5, which is the collapsible medical closure device 2 of FIG. 1 as viewed down cone shaped portion 8 of collapsible medical closure device 2, there is shown collapsible medical closure device 2, cone shaped portion 8, disc shaped portion 4, center end screw 30, and delivery cable 32. Delivery cable 32 is threadably attached to center end screw 30 such that collapsible medical closure device 2 would be ready to be collapsed and inserted into a delivery device (not shown) and inserted into a patient. Delivery cable 32 aids in the application of collapsible medical closure device 2 into a patient, the process of which is described in more detail below, after which delivery cable 32 is threadably disengaged and removed. Additionally, so long as delivery cable 32 is connected to center end screw 30, the operator may still retract collapsible medical closure device 2 back into a delivery vehicle (such as a delivery catheter, not shown) for repositioning or replacing if it is determined that collapsible medical closure device 2 is not properly positioned or sized in the first attempt.

Figure 6A:
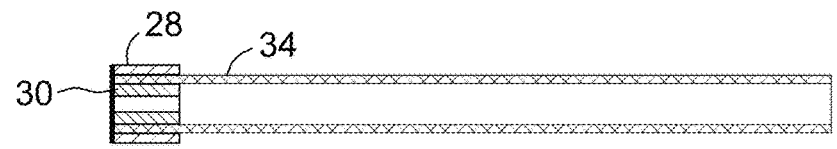
FIGS. 6A-6G are schematic cross-sections of the collapsible medical closure device of FIG. 1 at various stages of an exemplary method of manufacturing.

FIGS. 6A-6G provide schematic cross-sections of collapsible medical closure device 2 at various stages of an exemplary method of manufacturing. In one exemplary embodiment described herein, collapsible medical closure device 2 having disc shaped portion 4 on distal end 6 and cone shaped portion 8 on proximal end 10 separated by middle portion 12 (as shown in FIGS. 1 and 2) is constructed from tubular nitinol wire mesh material 34 as described above. Tubular nitinol wire mesh material 34 is selected having a diameter of about 0.076 millimeters and a number of wires in the nitinol wire mesh of 144. As shown in FIG. 6A, second radiopaque marker band 28 is placed over one end of tubular nitinol wire mesh material 34 and center end screw 30 is inserted into tubular nitinol wire mesh material 34 and second radiopaque marker band 28. Any portion of tubular nitinol wire mesh material 34 that extends past second radiopaque marker band 28 and center end screw 30 is trimmed flush with second radiopaque marker band 28 using a laser or other suitable trimming method. The circumference (not shown) of tubular nitinol wire mesh material 34, center end screw 30 and second radiopaque marker band 28 is then welded (using a laser or other suitable method) to circumferentially join tubular nitinol wire mesh material 34, center end screw 30 and second radiopaque marker band 28. In alternative embodiments, solder or braze may be used in place of welding for the joining.

Figure 6B:
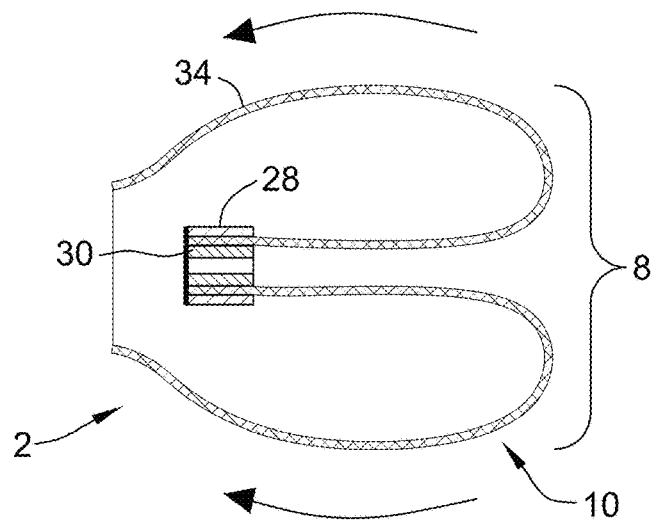
Figure 6C:
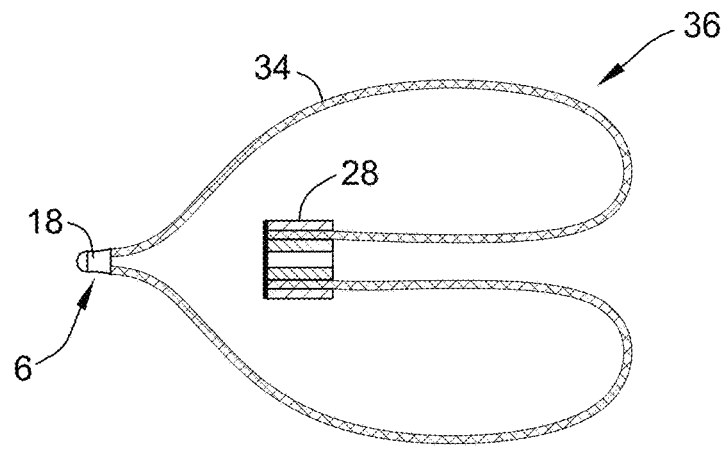

As shown in FIG. 6B, once tubular nitinol wire mesh material 34, center end screw 30, and second radiopaque marker band 28 are joined, tubular nitinol wire mesh material 34 is then inverted over joined tubular nitinol wire mesh material 34, center end screw 30, and second radiopaque marker band 28 to ultimately form cone shaped portion 8 on proximal end 10 of collapsible medical closure device 2 (as also shown in FIG. 1). Tubular nitinol wire mesh material 34 is then cut, and, as shown in FIG. 6C, first radiopaque marker band 18 is then placed on tubular nitinol wire mesh material 34 at distal end 6. The distance between first radiopaque marker band 18 and second radiopaque marker band 28 is then set to the desired length, which produces a cut to length 36. First radiopaque marker band 18 is then swaged to lock first radiopaque marker band 18 to tubular nitinol wire mesh material 34 and any excess tubular nitinol wire mesh material 34 is trimmed off. First radiopaque marker band 18 is then welded to produce a dome weld on cut to length 36. Alternatively, first radiopaque marker band 18 can be omitted and heat setting, soldering, brazing, welding, or the like can be used to prevent unraveling of tubular nitinol wire mesh material 34.

Figure 6D:
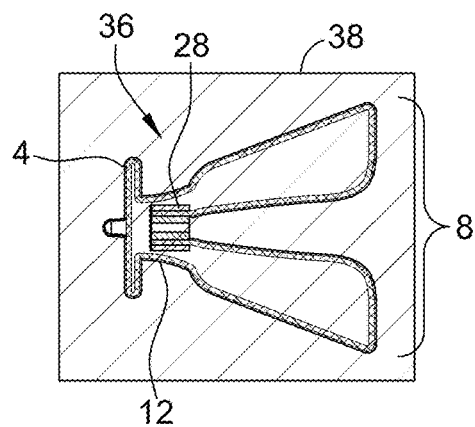

Referring now to FIG. 6D, once the dome weld is complete, cut to length 36 is placed into forming mold element 38. The shape of forming mold element 38 should be selected to deform the tubular nitinol wire mesh material into substantially the desired shape of the collapsible medical closure device (e.g., collapsible medical closure device 2 of FIGS. 1 and 2 having cone shaped portion 8, disc shaped portion 4, and middle portion 12). The loaded mold is then placed into an oven that heat sets the formed device including cone shaped portion 8, disc shaped portion 4, and middle portion 12 with second radiopaque marker band 28 positioned at least partially and desirably substantially within middle portion 12. Suitable heat treatments of tubular nitinol wire mesh are well known in the art. For example, holding a tubular nitinol wire mesh at about 500° C. to about 550° C. for a period of about 1 minute to about 30 minutes will tend to set the tubular nitinol wire mesh in its deformed state where it conforms to the mold. At lower temperatures the heat treatment time will generally be longer (e.g., about one hour at about 350° C.) and at higher temperatures the time will tend to be shorter (e.g., about 30 seconds at about 900° C.). After the heat treatment is complete, tubular nitinol wire mesh material 34 will substantially retain the desired shape of collapsible medical closure device 2 (as shown in FIG. 1).

Figure 6E:
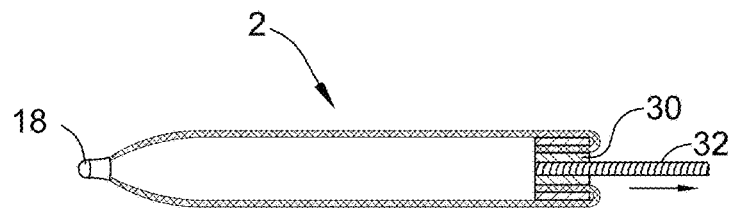

Once shaped, collapsible medical closure device 2 may have proximal and distal end therapeutic membranes 24 and 26 added thereto to improve the occlusion properties of collapsible medical closure device 2. In one embodiment, as shown in FIG. 6E, delivery cable 32 (as also shown in FIGS. 4 and 5) is threadably connected to center end screw 30 such that upon pulling delivery cable 32 in a direction opposite first radiopaque marker band 18, collapsible medical closure device 2 is pulled into an elongated form.

Figure 6F:
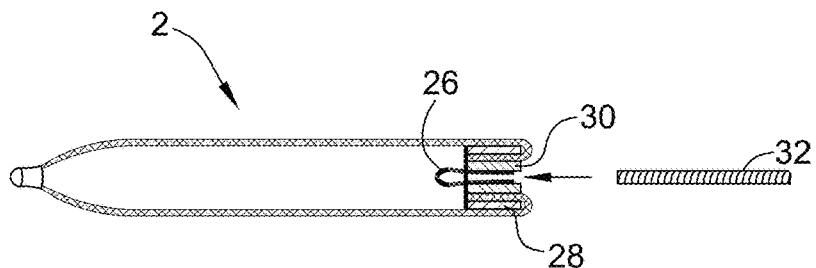

Referring now to FIG. 6F, once the elongation is formed, delivery cable 32 is removed and distal end therapeutic membrane 26, which as described above is disc shaped, is inserted through center end screw 30 and positioned within collapsible medical closure device 2 such that upon returning second radiopaque marker band 28 to its formed position within middle portion 12 of collapsible medical closure device 2 (as shown in FIG. 2), distal end therapeutic membrane 26 is positioned between top layer of metal fabric 5 and bottom layer of metal fabric 7 of disc shaped portion 4 as shown in FIG. 2.

Figure 6G:
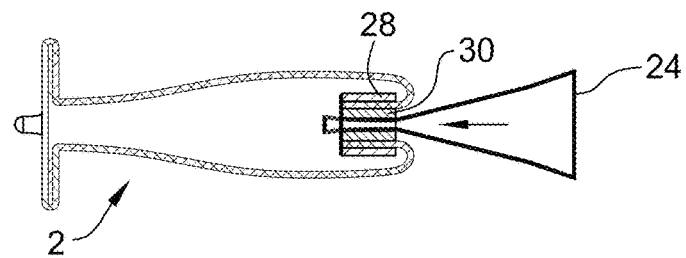

Now referring to FIG. 6G, proximal end therapeutic membrane 24 is then inserted through center end screw 30 and positioned within collapsible medical closure device 2 such that upon returning second radiopaque marker band 28 to its formed position within middle portion 12 (as shown in FIG. 2), proximal end therapeutic membrane 24 is sandwiched between first layer of metal fabric 20 and second layer of metal fabric 22 of cone shaped portion 8 and middle portion 12 as shown in FIG. 2.

As discussed above, to secure proximal and distal end therapeutic membranes 24 and 26 into position, the edges of proximal and distal end therapeutic membranes 24 and 26 may be tucked between the picks of tubular nitinol wire mesh material 34, and/or may be sewn into the tubular nitinol wire mesh material (as shown in FIG. 1) using a suitable thread material. As one skilled in the art will recognize based on the disclosure herein, a number of changes/additions/substitutions could be made in the above-described manufacturing process without departing from the spirit and scope of the present disclosure. The above-described manufacturing process is simply illustrative of one suitable method.

As discussed above, collapsible medical closure device 2 as described herein is well suited for use in medical procedures when rapid occlusion is desired followed by long-term occlusion. In one specific embodiment, collapsible medical closure device 2 is used to provide occlusion on the wall of the heart after a procedure that requires apical access to the left ventricle. In this embodiment, as well as in other embodiments, collapsible medical closure device 2 may be delivered and placed as described below using, for example, two dimensional echocardiography and Doppler color flow mapping for device guidance.

Figure 7A:
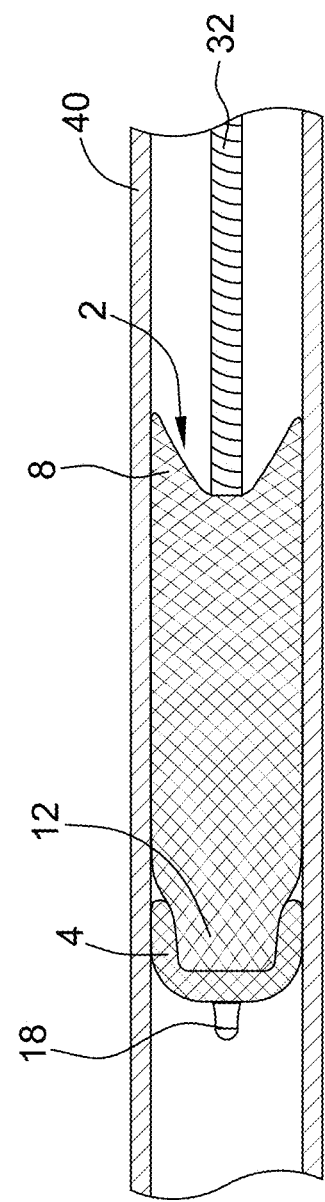
Figure 7C:
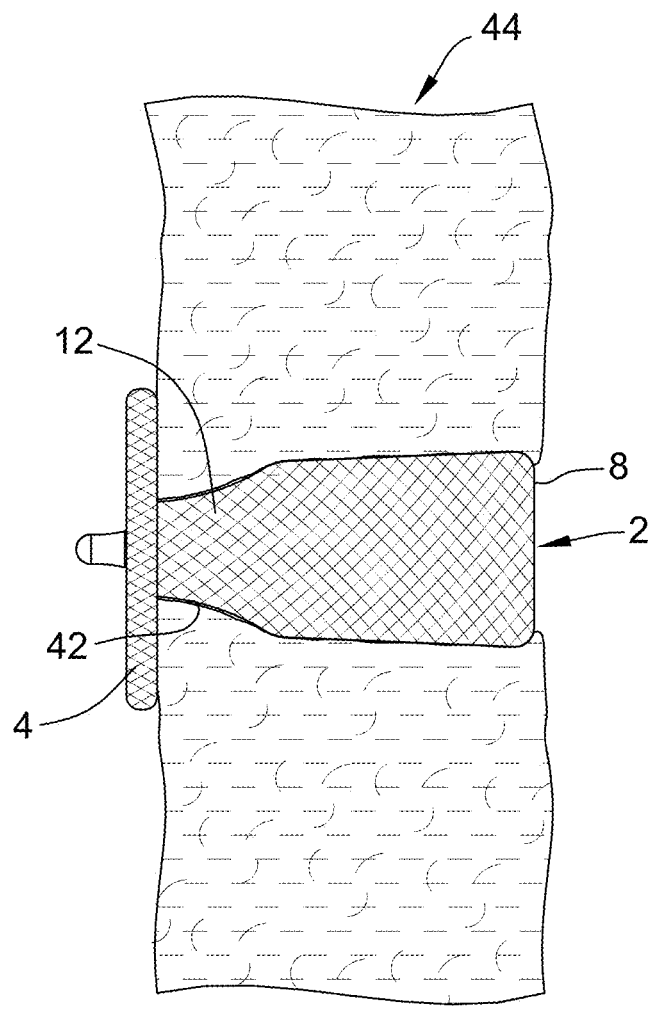

FIGS. 7A-7C are schematic views of collapsible medical closure device 2 at various stages of loading and placement into a heart wall. Specifically, as shown in FIG. 7A, collapsible medical closure device 2 including disc shaped portion 4, cone shaped portion 8, middle portion 12, and first radiopaque marker band 18, is attached to delivery cable 32 (e.g., by threaded attachment between delivery cable 32 and center end screw 30 as shown in FIGS. 4 and 5). Collapsible medical closure device 2 attached to delivery cable 32 is inserted into delivery catheter 40 to load collapsible medical closure device 2 in its collapsed for delivery configuration into delivery catheter 40 for insertion.

As shown in FIG. 7B, delivery catheter 40 is inserted into opening 42 of heart wall 44. Collapsible medical closure device 2 is then urged through delivery catheter 40 using delivery cable 32 until disc shaped portion 4 is positioned on interior heart wall 46 in its unconstrained, expanded state (as shown in FIG. 1) such that it comes into contact with interior heart wall 46 surrounding opening 42 to be occluded. Once disc shaped portion 4 has been fully ejected and expanded, delivery catheter 40 is pulled away from opening 42 and delivery cable 32 is used to urge middle portion 12 and cone shaped portion 8 from delivery catheter 40 until collapsible medical closure device 2 has been completely ejected from delivery catheter 40 and cone shaped portion 8 and middle portion 12 expand to contact the interior of opening 42 in heart wall 44, as shown in FIG. 7C. Collapsible medical closure device 2 may be partially or completely reloaded or recaptured within delivery catheter 40 and subsequently redeployed and/or repositioned as necessary to properly position collapsible medical closure device 2 so long as collapsible medical closure device 2 is attached to delivery cable 32. Once it has been determined by the operator that collapsible medical closure device 2 is properly positioned, delivery cable 32 is removed from center end screw 30 and collapsible medical closure device 2 is considered to be in its final position within the patient. The squeezing and pushing action on collapsible medical closure device 2 from the heart can pull disc shaped portion 4 tightly against opening 42 in heart wall 44, thus facilitating short-term and long-term occlusion of opening 42 and long term tissue growth.

Although a number embodiments of this disclosure have been described above with a certain degree of particularity, those skilled in the art could make numerous alterations to the disclosed embodiments without departing from the spirit or scope of the disclosure. For example, an important feature of this disclosure is the presence of the therapeutic membrane on the collapsible medical closure device. One skilled in the art may modify the number of layers, thickness of the layers, material of the layers and so on without departing from the spirit or scope of the disclosure. It is intended that all matter contained in the above description or shown in the accompanying drawings shall be interpreted as illustrative only and not limiting. Changes in detail or structure may be made without departing from the spirit of the disclosure as defined in the claims.

EXAMPLE

The following example illustrates a specific embodiment and/or feature of a collapsible medical closure device of the present disclosure. The example is given solely for the purpose of illustration and is not to be construed as a limitation of the present disclosure, as many variations thereof are possible without departing from the spirit and scope of the disclosure.

In this Example, a collapsible medical closure device of the present disclosure (similar to that shown in FIG. 1) was implanted into a porcine heart apex to evaluate device occlusion, device fit, and ease of device delivery. The wall thickness in the porcine was about 8 millimeters. The device was fabricated to have an overall length (corresponding to length L1 shown in FIG. 3) of about 8 millimeters, a cone shaped portion diameter (corresponding to diameter D2 shown in FIG. 3) of about 10 millimeters, and a disc shaped portion diameter (corresponding to diameter D1 shown in FIG. 3) of about 7 millimeters. The cone shaped portion of the collapsible medical closure device was comprised of two layers of nitinol (similar to first layer of metal fabric 20 and second layer of metal fabric 22 as shown in FIGS. 1 and 2) having a wire count of 144, and included a single layer therapeutic membrane constructed of a collagen sponge (similar to proximal and distal end therapeutic membranes 24 and 26 shown in FIGS. 1 and 2) sandwiched within the cone shaped portion and disc shaped portion of the collapsible medical closure device.

A median sternotomy was performed on the animal and the pericardial sac was opened. A 22 Fr Ultimum introducer was inserted into the left ventricle. The collapsible medical closure device described above was loaded into a delivery sheath (similar to delivery catheter 40 as shown in FIGS. 7A and 7B) and advanced into position until the disc shaped portion of the collapsible closure medical device was in its expanded configuration. Both the delivery sheath and collapsible medical closure device were pulled back until the disc shaped portion of the device was positioned against the ventricular wall. At this time, the rest of the collapsible medical closure device, including the cone shaped portion and the middle portion, was deployed with an unsheathing motion. The collapsible medical closure device was observed to deploy easily. After deployment, there was observed a very slight pulsed weeping of blood in the center of the cone shaped portion of the collapsible medical closure device; that is, a small amount of blood was noted to be penetrating through the cone shaped portion of the collapsible medical closure device.

Figure 8:
FIG. 8 is a photograph showing an implanted collapsible medical closure device of the present disclosure.

After the delivery cable was detached, the collapsible medical closure device was left and the implantation site monitored for 10 minutes. After about 5 minutes there was no further blood seen exiting at the access site, including at the cone shaped portion. FIG. 8 is a photograph showing the implanted collapsible medical closure device in the porcine beating heart five minutes after placement. Complete occlusion was noted at the implantation site and a tight fit around the cone shaped portion was observed. The cone shaped portion did not extend beyond the opening.

Figure 9:
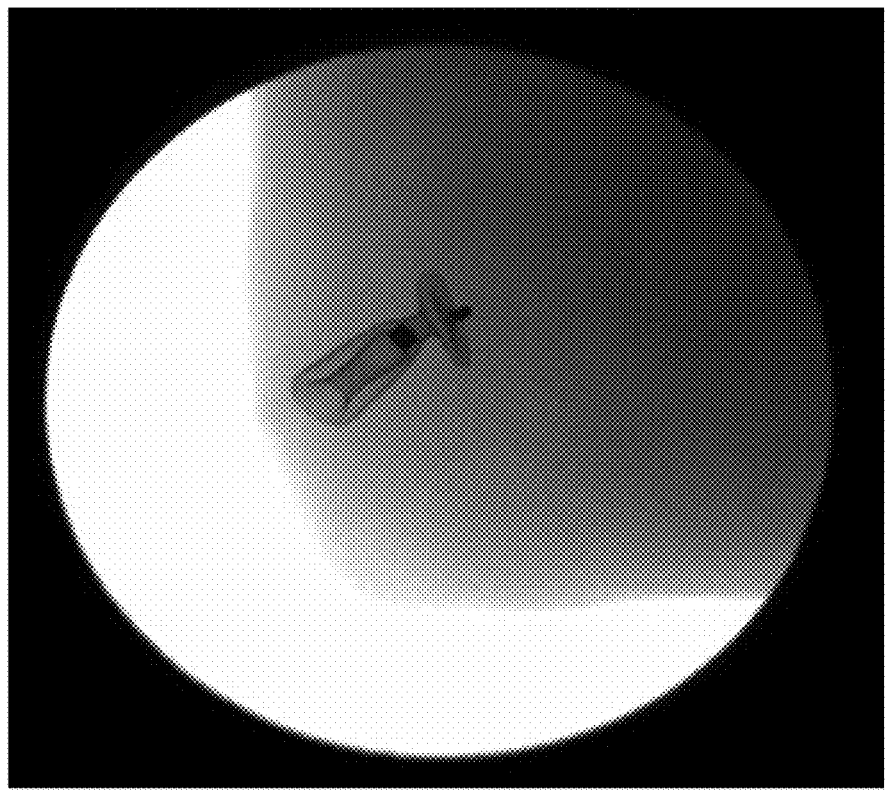
FIG. 9 is a Fluoroscan of an implanted collapsible medical closure device of the present disclosure.

The animal was sacrificed and the heart was harvested with the collapsible medical closure device in place. It was observed that the collapsible medical closure device was stable and the disc shaped portion fit into the left ventricle without significant compromise of nearby structures. FIG. 9 is a Fluoroscan of the collapsible medical closure device implanted into the porcine heart and shows stable placement of the collapsible medical closure device in the desired area.

What is claimed is:

1. A method of forming a collapsible medical closure device, the method comprising:
   introducing a radiopaque marker band onto one end of a tubular metal fabric formed from a plurality of metal strands being formed from a material that can be heat treated to substantially set a desired shape;
   introducing a means for attaching a delivery device inside of the radiopaque marker band;
   inverting the tubular metal fabric over itself;
   conforming the inverted tubular metal fabric to an internal surface of a molding element, the molding element including a disc shaped portion, a middle portion, and a cone shaped portion;
   heating the inverted tubular metal fabric;
   removing the tubular metal fabric from the molding element, whereby the tubular metal fabric defines the collapsible medical closure device having a disc shaped portion, a cone shaped portion, and a middle portion connecting the cone shaped portion and the disc shaped portion, wherein the middle portion contains the means for attaching a delivery device and the radiopaque marker band; and
   contacting a therapeutic membrane with the tubular metal fabric.

2. The method of claim 1 further including circumferentially joining the tubular metal fabric, the means for attaching a delivery device, and the radiopaque marker band before inverting the tubular metal fabric over itself.

3. The method of claim 2 wherein circumferentially joining the tubular metal fabric, the means for attaching a delivery device, and the radiopaque marker band comprises welding the tubular metal fabric, the means for attaching a delivery device, and the radiopaque marker band.

4. The method of claim 2 further including trimming a portion of the tubular metal fabric extending past the radiopaque marker band and the means for attaching a delivery device prior to circumferentially joining the tubular metal fabric, the means for attaching a delivery device, and the radiopaque marker band.

5. The method of claim 1 further including introducing a second radiopaque marker band onto the tubular metal fabric after the tubular metal fabric is inverted.

6. The method of claim 5 further including cutting the tubular metal fabric to a desired length after inverting the tubular metal fabric and prior to introducing the second radiopaque marker band onto the tubular metal fabric.

7. The method of claim 5 wherein introducing a second radiopaque marker band onto the tubular metal fabric includes swaging the second radiopaque marker band to lock the second radiopaque marker band to the tubular metal fabric.

8. The method of claim 7 further including trimming a portion of the tubular metal fabric extending from the second radiopaque marker band.

9. The method of claim 8 further including welding the second radiopaque marker band to produce a dome weld.

10. The method of claim 1 wherein contacting the therapeutic membrane with the tubular metal fabric includes connecting a delivery cable to the means for attaching a delivery device, pulling on the delivery cable in a direction opposite the second radiopaque marker band to elongate the tubular metal fabric, removing the delivery cable, inserting the therapeutic membrane through the means for attaching a delivery device, and positioning the therapeutic membrane within the tubular metal fabric.

11. The method of claim 10 wherein inserting the therapeutic membrane through the means for attaching a delivery device and positioning the therapeutic membrane within the tubular metal fabric includes inserting a first therapeutic membrane through the means for attaching a delivery device and positioning the first therapeutic membrane within the tubular metal fabric such that the first therapeutic membrane is positioned within the disk shaped portion of the collapsible medical closure device.

12. The method of claim 11 further including inserting a second therapeutic membrane through the means for attaching a delivery device and positioning the second therapeutic membrane within the tubular metal fabric such that the second therapeutic membrane is positioned within the cone shaped portion and the middle portion of the collapsible medical closure device.

13. The method of claim 12 further including securing the first therapeutic membrane to the disk shaped portion and securing the second therapeutic membrane to at least one of the cone shaped portion and the middle portion of the collapsible medical closure device.

14. The method of claim 13 wherein securing the first therapeutic membrane and the second therapeutic membrane includes at least one of tucking a portion of the first therapeutic membrane and the second therapeutic membrane between picks of the tubular metal fabric and sewing the first therapeutic membrane and the second therapeutic membrane to the tubular metal fabric.

\* \* \* \* \*